United States Patent [19]

Geffers et al.

[11] 4,020,101

[45] Apr. 26, 1977

[54] α-ALKYL-PHOSPHONOSUCCINIC ACID COMPOUNDS AND SEQUESTERING COMPOSITIONS CONTAINING THEM

[75] Inventors: Hans Geffers, Cologne; Walter Radt, Leverkusen; Reinhard Schliebs, Cologne; Hartmut Schulz, Leverkusen, all of Germany

[73] Assignee: Bayer Aktiengesellschaft, Leverkusen, Germany

[22] Filed: Jan. 20, 1975

[21] Appl. No.: 542,741

Related U.S. Application Data

[63] Continuation of Ser. No. 218,516, Jan. 17, 1972, abandoned.

[30] Foreign Application Priority Data

Mar. 28, 1970 Germany .................. 2015068

[52] U.S. Cl. .................. 260/502.4 R; 210/58; 252/82; 252/180; 260/501.21; 260/638 R; 260/961

[51] Int. Cl.$^2$ .................. C07F 9/38

[58] Field of Search .................. 260/502.4 R

[56] References Cited

UNITED STATES PATENTS

| | | | |
|---|---|---|---|
| 2,724,718 | 11/1955 | Stiles et al. .................. | 260/502.4 R |
| 3,021,279 | 2/1962 | Scanley .................. | 260/502.4 R |
| 3,236,863 | 2/1966 | Smith et al. .................. | 260/502.4 R |
| 3,293,176 | 12/1966 | White .................. | 260/502.4 R |

OTHER PUBLICATIONS

Pudovik, "Bull. Acad. Sci. USSR, Div. Chem. Sci.", 1952 (English Translation) pp. 821–824.

*Primary Examiner*—Joseph E. Evans
*Attorney, Agent, or Firm*—Burgess, Dinklage & Sprung

[57] ABSTRACT

Certain novel α-alkyl-phosphonosuccinic acid compounds of the formula

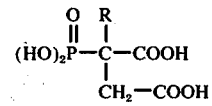

in which
R is lower alkyl, or alkenyl or alkynyl, cycloalkyl, or aralkyl are particularly suitable as sequestering agents, e.g., for incorporation into cleansing compositions.

7 Claims, No Drawings

α-ALKYL-PHOSPHONOSUCCINIC ACID COMPOUNDS AND SEQUESTERING COMPOSITIONS CONTAINING THEM

This is a continuation of application Ser. No. 218,516 filed Jan. 17, 1972, now abandoned.

This invention relates to novel compounds, to a process for making them, and to sequestration agents, for use in cleansing compositions, containing them.

The novel compounds of the invention are α-alkyl-phosphonosuccinic acid compounds of the formula:

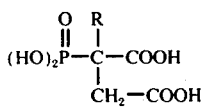  (I)

in which
R is lower alkyl, preferably alkyl of from 1 to 4 carbon atoms; or alkenyl or alkynyl of from, e.g. 2 to 4 carbon atoms; cycloalkyl, preferably of from 4 to 7 ring carbons; or aralkyl, e.g., of from 6 to 12 ring carbons and of from 1 to 4 alkyl group carbons.

The invention also relates to a process for the production of the α-alkyl-phosphonic acid compounds of the formula (I), which comprises alkylating a phosphonosuccinic acid ester of the formula:

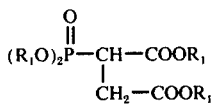  (II)

in which
$R_1$ is lower alkyl, e.g., of from 1 to 4 carbons, and subsequently acidically hydrolyzing the α-alkyl-phosphonosuccinic acid tetraalkyl esters obtained.

As exemplary of the alkyl definition for R there may be mentioned, in particular, alkyl radicals such as the methyl, ethyl, propyl, isopropyl, butyl, sec.-butyl, hexyl and 2-ethylhexyl radicals; of the alkenyl radicals, primarily the allyl and methallyl radicals; for the alkynyl radicals, primarily the propyn-(1)-yl-(3) radical; for the cycloalkyl radicals, cyclobutyl, cyclopentyl, cyclohexyl, and cycloheptyl; and of the aralkyl radicals, primarily the benzyl and methylbenzyl radicals.

As illustrative of the alkyl radicals embraced by $R_1$ there may be mentioned the methyl and ethyl radicals.

In carrying out the process of the invention, the alkylation of the phosphonosuccinic acid tetraalkyl ester is carried out by first metallizing the phosphonosuccinic acid tetraalkyl esters, for example, by reacting them with stoichiometric amounts of an alkali metal, such as lithium or potassium but preferably sodium, or with stoichiometric amounts of alkali metal compounds which are capable of forming salts with acidic compounds, e.g. alkali metal amides such as sodium amides; alkali metal hydrides, such as sodium hydride; or alkali metal alcoholates such as sodium methylate, sodium ethylate or potassium tert.-butylate; and by subsequently reacting the resultant alkali metal phosphonosuccinic acid tetraalkyl ester compounds with conventional alkylating agents such as alkyl halides, e.g. methyl bromide, methyl iodide, ethyl chloride, allyl bromide, methallyl chloride, butyl iodide, cyclohexyl bromide, benzyl chloride; dialkyl sulphates such as methyl sulphate and ethyl sulphate; alkyl-sulphonic acid esters such as p-toluene-sulphonic acid ester; trialkyl phosphates such as trimethyl phosphate or triethyl phosphate. The phosphonosuccinic acid tetraalkyl esters can also be used as alkylating agents.

The metallization and alkylation of the phosphonosuccinic acid tetraalkyl esters is preferably carried out in inert organic solvents such as aromatic hydrocarbons, e.g. benzene, toluene, xylene; or others, e.g. ether, tetrahydrofuran. The metallization usually proceeds with a positive heat effect. Cooling may therefore be necessary. The alkylation is carried out at temperatures between 10° and 180° C, preferably between 20° and 140° C. The resultant α-alkyl-phosphonosuccinic acid tetraalkyl ester can subsequently be purified by vacuum distillation.

Alkylation of the phosphonosuccinic acid tetraalkyl esters with phosphonosuccinic acid tetraalkyl esters yields mixtures of phosphonosuccinic acid trialkyl esters, tetraalkyl esters, α-alkyl-phosphonosuccinic acid trialkyl esters and tetraalkyl esters or their sodium salts. The alkylation is carried out by reacting phosphonosuccinic acid tetraalkyl esters with alkali metal alhoholates or alkali metals at 80°–170° C, preferably at 100°–150° C. The amount of alkali metal alcoholate or alkali metal is decisive for the proportion of α-alkyl-phosphonosuccinic acid alkyl ester in the mixtures. If 0.5 mol alkali metal or alcoholate is used for every mol of phosphonosuccinic acid tetraalkyl ester, a mixture is obtained which consists of about 50% α-alkylated and about 50% non-alkylated phosphonosuccinic acid alkyl esters. If one mol alkali metal or alcoholate is used for every mol of phosphonosuccinic acid tetraalkyl ester, the mixture substantially consists of α-alkylated phosphonosuccinic acid trialkyl esters.

The resultant α-alkyl-phosphonosuccinic acid alkyl esters are subsequently hydrolyzed by heating with concentrated hydrochloric acid. The hydrolysis can also be carried out in two stages by first partially hydrolyzing the esters with dilute aqueous hydrochloric acid while the liberated alcohol is distilled off and subsequently completing the hyrolysis by the addition of concentrated hydrochloric acid.

After hydrolysis, the α-alkyl-phosphonosuccinic acids are in the form of their solution in hydrochloric acid. When the hydrochloric acid is distilled off in a vacuum at temperatures up to about 140° C, there are obtained the anhydrous α-alkyl-phosphonosuccinic acids which are viscous in the hot and either crystallize or solidify to form a glassy mass in the cold.

The following examples are illustrative of the process of this invention.

EXAMPLE 1

Preparation of α-methyl-phosphonosuccinic acid 254 g (1 mol) phosphonosuccinic acid tetramethyl ester were added dropwise at 20°–25° C with intense stirring and good cooling to a suspension of 23 g (1 mol) sodium in 300 ml toluene. A clear yellow solution of sodium-phosphonosuccinic acid tetramethyl ester in toluene was formed.

126 g (1 mol) dimethyl sulphate were added dropwise at 10°–40° C within about 25 minutes to this solution while stirring and cooling. Stirring of the reaction mixture was subsequently continued for 1 hour. The precipitated sodium monomethyl sulphate was then filtered off and the filtrate was freed from the solvent by distillation in a vacuum up to a sump temperature of about 60° C. The crude α-methyl-phosphonosuccinic acid tetramethyl ester was subsequently fractionally distilled. Yield 172 g (65% of theory); b.p. 127°–130° C/1 mm Hg.

The α-methyl-phosphonosuccinic acid tetramethyl ester so obtained was heated at boiling temperature with 100 ml of dilute hydrochloric acid (2 mol HCL/liter) for 18 hours while the methanol formed in the hydrolysis was distilled off. The hydrolysis mixture was subsequently mixed with 150 ml of concentrated hydrochloric acid (12 mol HCl/liter) and heated at reflux temperature for a further 18 hours. The reaction solution was then evaporated to dryness in a vacuum (maximum sump temperature 120° C) and diluted with water to form a 50% solution of the title compound.

EXAMPLE 2

Preparation of a mixture of α-methyl-phosphonosuccinic acid and phosphonosuccinic acid 254 g (1 mol) phosphonosuccinic acid tetramethyl ester were mixed at 20°–25° C, while stirring, with a solution of 54 g (1 mol) sodium methylate in 330 ml methanol. After the addition of 300 ml toluene, the solvent mixture was distilled off in a vacuum at 15°–25° C to such an extent that the sodium phosphonosuccinic acid tetramethyl ester just remained dissolved. After adding another 300 ml toluene and again distilling off the solvent mixture in a vacuum, the sodium salt was present in a toluene solution almost free from methanol.

The solution of the sodium-phosphonosuccinic acid tetramethyl ester so obtained was mixed dropwise at 20°–30° C within 30 minutes, while stirring and cooling, with 140 g (1 mol) trimethyl phosphate. The reaction mixture was subsequently stirred for a further 2 hours. The precipitated sodium dimethyl phosphate was then filtered off and the filtrate was freed from the solvent by distillation in a vacuum up to a sump temperature of 60° C. The crude product was subsequently purified by distillation. Yield 195 g; b.p. 126°–131° C/1 mm Hg.

According to its gas chromatogram, the distillation product cnsisted of 86% α-methyl-phosphonosuccinic acid tetramethyl ester and 10% phosphonosuccinic acid tetramethyl ester.

The distillation product was heated with 400 ml of concentrated hydrochloric acid (12 mol/liter) at reflux temperature for 24 hours. The reaction solution which was still weakly acidic was subsequently evaporated to dryness in a vacuum up to a sump temperature of 120° C, and then diluted with water to form a 50% solution of the title compounds.

EXAMPLE 3

Preparation of α-allyl-phosphonosuccinic acid

To a solution of 1 mol sodium-phosphonosuccinic acid tetramethyl ester in 200 ml toluene prepared as described in Example 1 there were added at 20°–25° C within about 20 minutes with stirring and cooling 121 g (1 mol) allyl bromide. When the addition of allyl bromide was completed, stirring was continued for 3 hours. The precipitated sodium bromide was filtered off and the filtrate was freed from the solvent by distillation in a vacuum up to a sump temperature of 60°–70° C. The crude product was subsequently distilled. Yield 246 g (84% of theory); b.p. 133°–140° C/1 mm Hg.

According to the gas chromatogram, the product contained 92% α-allyl-phosphonosuccinic acid tetramethyl ester.

The ester was hydrolyzed in the manner described in Example 1 to form the title compound.

EXAMPLE 4

Preparation of a mixture of phosphonosuccinic acid and α-methyl-phosphonosuccinic acid A solution of 27 g (0.5 mol) sodium methylate in 180 ml methanol was added dropwise at 100° C with stirring and heating within about 90 minutes to 254 g (1 mol) phosphonosuccinic acid tetramethyl ester. The evaporating methanol was distilled off. When the addition of methylate was completed, the reaction mixture was stirred at 100° C for 30 minutes. The reaction product was then allowed to cool to 50° C, and 42 ml of concentrated hyrochloric acid (12 mol HCl/liter) were added dropwise. The precipitated sodium chloride was subsequently filtered off. The filtrate was hydrolyzed in the manner described in Example 1. There were obtained 360 g of 50% aqueous solution of a 1:1 mixture of phosphonosuccinic acid and α-methyl-phosphonosuccinic acid.

EXAMPLE 5

Preparation of a mixture of phosphonosuccinic acid and α-methyl-phosphonosuccinic acid A solution of 40.5 g (0.75 mol) sodium methylate in 270 ml methanol was added dropwise at 135° C within 30 minutes with stirring and heating to 254 g (1 mol) phosphonosuccinic acid tetramethyl ester. The evaporating methanol was distilled off in a water jet vacuum during the dropwise addition. The reaction mixture was subsequently further stirred for 30 minutes at 135° C under normal pressure. After cooling to about 50° C, the reaction product was mixed with 63 ml (0.75 mol) of concentrated hydrochloric acid, and the precipitated sodium chloride was filtered off. The filtrate was hydrolyzed in the manner described in Example 1.

After concentration of the hydrolysis solution in a vacuum, there were obtained 150 g of 1:3 mixture of phosphonosuccinic acid and α-methyl-phosphonosuccinic acid.

EXAMPLE 6

Preparation of a mixture of phosphonosuccinic acid and α-methyl-phosphonosuccinic acid 27 g (0.5 mol) of solid sodium methylate were introduced in portions of 3.5 g with stirring and cooling within 30 minutes at 100° C into 254 g (1 mol) of phosphonosuccinic acid tetramethyl ester which had been heated to 100° C. Each addition had to wait until the temperature of the mixture had fallen to 100° C. When the addition was completed the reaction mixture was further stirred for 1 hour.

The reaction mixture was worked up in the manner described in Example 5. A 1 : 1 mixture of phosphonosuccinic acid and α-methyl-phosphonosuccinic acid was obtained.

EXAMPLE 7

Preparation of a mixture of phosphonosuccinic acid and α-methyl-phosphonosuccinic acid 11.5 g (0.5 mol) sodium were introduced within 1 hour portionwise into a boiling mixture of 254 g (1 mol) phosphonosuccinic acid tetramethyl ester and 16 g methanol. The sodium melted and reacted with the mixture. After the last addition of sodium, stirring was continued for 1 hour at 120° C.

The reaction mixture was worked up in the manner described in Example 5. A 1 : 1 mixture of phosphonosuccinic acid and α-methyl-phosphonosuccinic acid was obtained.

EXAMPLE 8

Preparation of a mixture of phosphonosuccinic acid (methyl ester) and α-methyl phosphonosuccinic acid methyl ester The reaction of phosphonosuccinic acid tetramethyl ester with sodium methylate can also be carried out in a continuous operation. As reaction vessel there was used a refined steel reactor of 4.5 liters capacity which was fitted with a heatable jacket and with apertures for stirrer, internal thermometer, for the addition of the methylate solution and phosphonosuccinic acid methyl ester and for the removal of the reaction product and the methanol vapour. The heating jacket was charged with oil at 280° – 310° C via a thermostat with circulating pump. Phosphonosuccinic acid tetramethyl ester (41.1 mol/h, corr. to 10.46 kg/h) and a methylate solution with a content of 2.8 mol sodium methylate/liter methanol (20.5 mol/h = 7.2 liters of solution /h) were added with intense stirring by means of two dosing pumps. The evaporating methanol was condensed in a product cooler. The reaction temperature in the refined steel reactor was about 115° – 120° C. The reaction product, a mixture of phosphonosuccinic acid methyl ester or its sodium salt and α-methyl-phosphonosuccinic acid methyl ester or its sodium salt was reheated in a 4 liter-flask at 120° C.

Working up of the resultant reaction mixture was carried out in the manner described in Example 5. A 1 : 1 mixture of phosphonosuccinic acid and α-methyl-phosphonosuccinic acid was obtained.

EXAMPLE 9

Preparation of a mixture of phosphonosuccinic acid and α-ethyl phosphonosuccinic acid A solution of 34 g (0.5 mol) sodium ethylate in 185 ml ethanol was added dropwise at 150° C with stirring and heating within 2 hours to 310 g (1 mol) phosphonosuccinic acid tetraethyl ester. The evaporating ethanol was distilled off. When the addition of ethylate was completed, the reaction mixture was further stirred for 10 minutes.

The reaction mixture was worked up in the manner described in Example 5. There were obtained 375 g of a 50% aqueous solution of a 1 : 1 mixture of phosphonosuccinic acid and a α-ethyl-phosphonosuccinic acid.

EXAMPLE 10

Preparation of α benzyl phosphonosuccinic acid 126 g (1 mol) benzyl chloride were added dropwise at 30° –40° C with stirring to a solution of 1 mol sodiumphosphonosuccinic acid tetramethyl ester in 200 ml toluene prepared as described in Example 1. The reaction mixture was further stirred at the stated temperature for 4 hours. The reaction mixture was subsequently mixed with a solution of 1 mol hydrogen chloride in 250 ml of anhydrous ether. The precipitated sodium chloride was filtered off, and the filtrate was freed from all volatile compounds by distillation in a vacuum up to a sump temperature of 80° C. The crude product substantially consisted of α-benzyl-phosphonosuccinic acid methyl ester which was contaminated with phosphonosuccinic acid methyl ester and α-methyl-phosphonosuccinic acid methyl ester.

The crude product was hydrolyzed in the manner described in Example 1, to form the title compounds.

EXAMPLE 11

Preparation of a mixture of phosphonosuccinic acid (butyl ester) and α-butyl-phosphonosuccinic acid (butyl ester)

422 g (1 mol) phosphonosuccinic acid tetrabutyl ester were added dropwise at 20° – 30° C with intense stirring and good cooling to a suspension of 23 g (1 mol) sodium in 300 ml toluene. A clear solution of sodium phosphonosuccinic acid tetrabutyl ester in toluene was formed.

184 g (1 mol) butyl iodide were added dropwise to this solution at 80° C within 1 hour while stirring. The reaction mixture was subsequently further stirred at 80° C for 2 hours. The precipitated sodium iodide was filtered off, and the filtrate was freed from the volatile compounds by distillation in a vacuum up to a sump temperature of 100° C. According to the NMR spectrum the remaining crude product was a 1 : 9 mixture of phosphonosuccinic acid butyl ester and α-butyl-phosphonosuccinic acid butyl ester.

The mixture was hydrolyzed in the manner described in Example 1, to form the title acids.

EXAMPLE 12

Preparation of α-ethyl-phosphonosuccinic acid (tetraethyl ester)

154 g (1 mol) diethyl sulphate were added dropwise at 60° – 70° C within 30 minutes to a solution of 1 mol sodium-phosphonosuccinic acid tetraethyl ester in 200 ml toluene. The reaction mixture was further stirred for 1 hour. The precipitated sodium monoethyl sulphate was subsequently filtered off. The filtrate was freed from the toluene by distillation in a vacuum up to a sump temperature of 70° C. The resultant α-ethyl-phosphonosuccinic acid tetraethyl ester was hydrolyzed in the manner described in Example 1, to form the title acid.

The α-alkyl-phosphonosuccinic acids of the formula (I) were characterized by an excellent capability of forming complexes with alkaline earth metal ions. They are therefore eminently suitable as sequestration agents, e.g. in cleaning agents, such as are used in the food industry for cleaning bottles. The capability of the α-alkyl-phosphonosuccinic acids according to the invention of forming complexes is substantially higher than that of the phosphorus compounds hitherto used as sequestration agents. For example, the softening factor, which is a measure for the sequestration power of a compound, is as follows for certain illustrative compounds:

| Compound | Softening factor |
|---|---|
| β-phosphonobutyric acid | 26 |
| β-phosphonopropionic acid | 30 |
| 1-phosphonopropane-2,3-dicarboxylic acid | 58 |
| sodium hexametaphosphate | 100 |
| 1,2-diphosphonosuccinic acid | 100 |

-continued

| Compound | Softening factor |
| --- | --- |
| phosphonosuccinic acid | 100 |
| hydroxy-ethane-diphosphonic acid | 280 |
| nitrilo-trismethylene-phosphonic acid | 309 |
| α-methyl-phosphonosuccinic acid | 500 |

The softening factor was determined as follows:

Reagents:

1. sodium carbonate solution 100 g of calcined sodium carbonate p.a. were dissolved in distilled water and the solution was made up to 1000 ml.

2. calcium chloride solution 37.92 g $CaCl_2 \cdot H_2O$ were dissolved in distilled water and the solution was made up to 1000 ml.

Method of titration:

100 ml of the 1% test solution in distilled water were adjusted with sodium hydroxide or HCl to pH 13.0. 2 ml of sodium carbonate solution were added. The $CaCl_2$ solution was added dropwise with continuous stirring, until a cloudiness was detected, which did not dissolve within one minute. The calcium chloride solution was so adjusted that sodium hexametaphosphate gave a consumption of 10.0 ml of calcium chloride solution. The consumption of 0.1 ml of $CaCl_2$ solution corresponds to a softening factor of 1.

Consequently, sodium hexametaphosphate consuming 10.0 ml of $CACl_2$ solution had a softening factor of 100.

The α-alkyl-phosphonosuccinic acids according to the invention have the further advantage that the saturation concentration of their sparingly soluble calcium salts is not reached with the degrees of water hardness occurring in practice, whereas the saturation concentration of the sparingly soluble calcium salts of the known phosphoric acid or phosphonic acid sequestration agents is already reached with the usual degree of water hardness.

The critical calcium concentrations for a number of phosphoric and phosphonic acids are stated in the following Table (in ° German hardness).

| Compound | Critical Calcium Concentration | | |
| --- | --- | --- | --- |
| hydroxy-ethane-diphosphonic acid | 10° | German | hardness |
| phosphonosuccinic acid | 19° | " | " |
| nitrilo-trismethylene-phosphonic acid | 24° | " | " |
| Na-hexametaphosphate | 25° | " | " |
| α-methyl-phosphonosuccinic acid | 79° | " | " |

The α-alkyl-phosphonosuccinic acids according to the invention can be used as free acids or in the form of their alkali metal or amine salts in cleaning agents which may also contain conventional additives such as wetting agents, emulsifiers, anti-foaming agents, organic builders, bleaching agents an disinfectants.

The following examples are illustrative of this utility.

EXAMPLE 13

In a lemonade factory bottles were cleaned with a liquor containing 2% of caustic soda and an addition of 0.1% of the following concentrate of active ingredient:
10% o-phosphoric acid
10% α-methyl-phosphonosuccinic acid 10% of anti-foaming agent 70% of water.

The carbonate hardness of the water amounted to 15° German hardness. After removal, the bottles were perfectly clean and had no lime film; no lime deposits appeared in the cleaning machine.

EXAMPLE 14

In a brewery the bottles were cleaned with a liquor consisting of
1.00% of caustic soda
0.03% orthophosphate
0.04% of a mixture of phosphonosuccinic acid and α-methyl-phosphonosuccinic acid 1 : 1
0.02% of anti-foaming agent.

The total hardness amounted to 85° German hardness. The bottles were perfectly clean, free from any lime film and well wetted. In contrast to the use of polyphosphate-containing cleaning agents, no formation of scale was detected on the machine parts.

EXAMPLE 15

In a mineral warer factory, 10 ppm of a 1 : 1 mixture of phosphonosuccinic acid and α-methyl-phosphonosuccinic acid were added to the after-spray water having a temperature of 45° C. Scaling of the after-spray zone could thus be completely obviated and the percentage of bottles which bubbled over due to the liberation of $CO_2$ dropped to nil, since no more lime crystals which were the cause of the undesirable liberation of $CO_2$ were deposited in the bottles.

It will be understood that the specification and examples are illustrative but not limitative of the present invention and that other embodiments within the spirit of scope of the invention will suggest themselves to those skilled in the art.

What is claimed is:

1. α-Alkyl-phosphonosuccinic acid compound of the formula

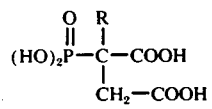

in which R is lower alkyl, or lower alkenyl or lower alkynyl.

2. Compound as claimed in claim 1 wherein R is alkyl of from one to four carbon atoms.

3. Compound as claimed in claim 1 wherein R is lower alkenyl or lower alkynyl of from two to four carbon atoms.

4. Compound as claimed in claim 1 designated α-methyl phosphonosuccinic acid.

5. Compound as claimed in claim 1 designated α-ethyl phosphonosuccinic acid.

6. Compound as claimed in claim 1 designated α-allyl-phosphonosuccinic acid.

7. Compound as claimed in claim 1 designated α-butyl-phosphonosuccinic acid.

* * * * *